United States Patent
Levitz et al.

(10) Patent No.: US 9,999,257 B2
(45) Date of Patent: Jun. 19, 2018

(54) BATTERY CONNECTOR FOR ELECTRONIC CIGARETTE WITH SIDE AIR INTAKE

(71) Applicant: SIS Resources Ltd., Beit Shemesh (IL)

(72) Inventors: Robert Levitz, North Miami Beach, FL (US); Shmuel Gavrielov, North Miami Beach, FL (US)

(73) Assignee: SIS RESOURCES, LTD., Beit Shemesh (IL)

( * ) Notice: Subject to any disclaimer, the term of this patent is extended or adjusted under 35 U.S.C. 154(b) by 0 days. days.

(21) Appl. No.: 15/492,290

(22) Filed: Apr. 20, 2017

(65) Prior Publication Data

US 2017/0215482 A1 Aug. 3, 2017

Related U.S. Application Data

(63) Continuation of application No. 14/051,029, filed on Oct. 10, 2013, which is a continuation of application No. PCT/US2012/033329, filed on Apr. 12, 2012.
(Continued)

(51) Int. Cl.
*A24F 47/00* (2006.01)
*A61M 11/04* (2006.01)
(Continued)

(52) U.S. Cl.
CPC .......... *A24F 47/008* (2013.01); *A61M 11/042* (2014.02); *F16B 7/0446* (2013.01);
(Continued)

(58) Field of Classification Search
CPC ... A24F 47/002; A24F 47/008; A61M 11/042; A61M 15/06; A61M 2016/0021;
(Continued)

(56) References Cited

U.S. PATENT DOCUMENTS 272,315 A * 2/1883 Pease .................. F16L 27/0812
285/280
3,797,865 A 3/1974 Ballentine
(Continued)

FOREIGN PATENT DOCUMENTS

CA 2641869 A1 5/2010
CN 201072979 6/2008
(Continued)

OTHER PUBLICATIONS

Specification Translation of CN 101843368. Chen, Zhiping. Suction nozzle of electronic atomizer. Sep. 29, 2010.*
(Continued)

*Primary Examiner* — Josh Skroupa
(74) *Attorney, Agent, or Firm* — Harness, Dickey & Pierce, P.L.C.

(57) ABSTRACT

The cylindrical connector includes a major body, the major body defining a longitudinal channel through a longitudinal length of the major body from a proximal portion through a distal portion, the proximal portion including a shaft with side walls. The connector further includes a flange located between the proximal portion and the distal portion, the flange at least partially defining at least a first portion of at least one first aperture in communication with the longitudinal channel. A distal portion of the major body being configured to attach to the first section of the e-vaping device and the proximal portion of the major body being configured to attach to the second section of the e-vaping device in order to define an airflow path that enters the longitudinal channel through the at least one first aperture and flows through the proximal portion of the major body.

18 Claims, 10 Drawing Sheets

Related U.S. Application Data

(60) Provisional application No. 61/474,569, filed on Apr. 12, 2011.

(51) Int. Cl.
    *F16B 7/04*     (2006.01)
    *F16B 7/18*     (2006.01)
    *H01R 33/22*     (2006.01)

(52) U.S. Cl.
    CPC .............. *F16B 7/182* (2013.01); *H01R 33/22* (2013.01); *Y10T 403/255* (2015.01); *Y10T 403/556* (2015.01); *Y10T 403/56* (2015.01)

(58) Field of Classification Search
    CPC .. A61M 2016/0039; A61M 2205/3653; A61M 2205/42; A61M 2205/8206; F16B 7/0406–7/0426; F16B 7/0446; F16B 7/182; Y10T 403/25; Y10T 403/255; Y10T 403/55; Y10T 403/556; Y10T 403/559; Y10T 403/56; Y10T 403/5761; Y10T 403/68; Y10T 403/7026
    USPC ... 403/34, 37, 292, 296, 298, 299, 309, 343, 403/359.1
See application file for complete search history.

(56) References Cited

U.S. PATENT DOCUMENTS

| | | |
|---|---|---|
| 4,947,875 A | 8/1990 | Brooks et al. |
| 2009/0272379 A1 | 11/2009 | Thorens et al. |
| 2011/0036346 A1 | 2/2011 | Cohen et al. |

FOREIGN PATENT DOCUMENTS

| | | |
|---|---|---|
| CN | 101843368 A | 9/2010 |
| CN | 101869356 A | 10/2010 |
| CN | 201767029 U | 3/2011 |
| JP | 2009537119 A | 10/2009 |
| JP | 2010213579 A | 9/2010 |
| JP | 2012124081 A | 6/2012 |
| WO | WO-98/43019 A1 | 10/1998 |
| WO | WO-2013116571 A1 | 8/2013 |

OTHER PUBLICATIONS

Specification Translation of CN 201072979. Li, Yonghai. Atomizer used for electronic cigarette. Jun. 18, 2008.*
International Search Report and Written Opinion of the International Searcing Authority for corresponding PCT Application No. PCT/US2012/033329 dated Oct. 4, 2012.
International Preliminary Report on Patentability for corresponding PCT Application No. PCT/US2012/033329 dated Oct. 15, 2013.
International Search Report and Written Opinion of the International Searcing authority for corresonding PCT Application No. PCT/US2012/033329 dated Oct. 4, 2012.
International Preliminary Report on Patentability for corresponing PCT Application No. PCT/US2012/033329 dated Oct. 15, 2013.
Search Report for European Application No. 14170502.0 dated Feb. 25, 2015.
Office Action from corresponding Chinese Patent Application No. 201280018281.2, dated Jul. 1, 2015.
Supplementary European Search Report dated Feb. 12, 2015 for Application No. EP 12 77 1732.
Office Action from corresponding Japanese Patent Application 2014-505283, dated Jan. 18, 2016.
Office Action from U.S. Appl. No. 14/051,029, dated Mar. 2, 2016.
Office Action from U.S. Appl. No. 14/051,029, dated Jun. 2, 2016.
Office Action from U.S. Appl. No. 14/051,029, dated Dec. 7, 2016.
Notice of Allowance from U.S. Appl. No. 14/051,029, dated Feb. 15, 2017.
Extended European Search Report dated Feb. 25, 2015 for European Application No. 12771732.

\* cited by examiner

BATTERY CONNECTOR FOR ELECTRONIC CIGARETTE WITH SIDE AIR INTAKE

PRIORITY CLAIM

This application is a Continuation of U.S. application Ser. No. 14/051,029, filed Oct. 10, 2013, which claims priority as a Continuation to PCT Application No. PCT/US2012/033329, filed on Apr. 12, 2012, which claims priority to U.S. Provisional Patent Application No. 61/474,569, filed on Apr. 12, 2011, each of which are incorporated by reference in their entirety.

TECHNICAL FIELD

This invention relates generally to electronic cigarettes and more specifically to a battery connector for an electronic cigarette having a side air intake for improved air in-flow and out-flow through the electronic cigarette.

BACKGROUND

Electronic cigarettes are becoming a popular alternative to tobacco smoking because of the many advantages that they offer. One of the main reasons that they are popular is due to their similarities to tobacco smoking. In fact, the closer that they are in providing the experience of a traditional cigarette, the more likely they are to be accepted in the market place.

An electronic cigarette typically comprises a battery, an atomizer, a container of smoke juice, a heating element and a power control circuit. The battery is used to power the circuit and the atomizer, where the atomizer heats the smoke juice to create smoke or vapor, which is inhaled by a user.

One example of an electronic cigarette (hereinafter an "Electronic Cigarette" or "E-cigarette") is a "two-piece" device having a first battery section and a second atomizer section, wherein the atomizer section is detachable from the battery section.

An example of one such Electronic Cigarette is shown in FIGS. 1 and 2. In some embodiments, the battery section B contains a power cell, an airflow sensor, and a chipset (hereinafter referred to as, the Battery). In some embodiments, the atomizer section A contains a heating element and a container of "smoke juice" which comprises flavorings and a vaporizing base, such as glycol (hereinafter referred to as a "Cartomizer"). Typically, the Battery and Cartomizer are physically and electrically connected by a threaded engagement. In some embodiments, the Battery has the "male" threaded portion and the Cartomizer has the "female" threaded portion, as shown in FIG. 2.

In the beginning stages of development of the Electronic Cigarette, it was natural to copy the air flow and to mimic its path similar to the way it behaves in a traditional cigarette. In a tobacco cigarette, air enters the tip, which collects the smoke and enters the smoker's mouth through the "filter." Likewise, early E-cigarettes had one or more notches at the tip of the Battery to allow air intake. Air would enter from the tip, pass through the entire Battery, and continue through the Cartomizer, the vapor-producing portion of the E-cigarette, and enter the smoker's mouth via the distal end of the Cartomizer, which functions as a mouth piece.

A cross-section of an example of this arrangement can be seen in FIG. 3. As shown in FIG. 3, when air 104 is inhaled through the mouthpiece 100, air enters the tip of the cigarette, travels past an air flow sensor 102 through the spaces provided around the sensor 102, and continues past the battery B (in this case a lithium cell.) It then goes through the opening in the axis of a post engaged with the Battery's male connector 106, and straight into a post 108 engaged to the female connector of the Cartomizer. The air is then inundated with atomized particles of liquid vapor and exits through the mouthpiece of the Cartomizer into the smoker's mouth.

Heretofore, there has often been a specific problem with tip-intake Electronic Cigarettes that the present invention aims to eliminate. When the smoker exhales into a tip-intake battery Electronic Cigarette (as smokers often do), the vapors 104A from the mouth follow the reverse of the path described above—they flow inside the Battery towards the sensor and often condense causing the sensor to become clogged and fail. The exhalation likewise causes excess liquid in the Cartomizer to follow the same path into the Battery part towards the sensor, clogging it further and also causing it to fail. This also causes major difficulties in mass-production in terms of maintaining consistent air flow and consistent sensitivity of the sensor from one Electronic Cigarette to the next.

Therefore it is desirable to avoid bringing the intake air through the entire length of the Battery through its rear tip (hereinafter "Tip-Intake"), and instead to bring it in through its front side (hereinafter "Side-Intake"), at the point where the Battery and Cartomizer sections meet.

However, it was always perceived as a necessity for the female threaded portion of the Cartomizer to have air slits at its edges when used in conjunction with a Side Intake Battery, because it was otherwise difficult to mass-produce machined male threads that allow air intake at its base. As a result, if it was desirable to change the design of the E-cigarette from the Tip-Intake type to the Side-Intake type, one would necessarily need to modify the female portion of the E-cigarette, i.e. the Cartomizer. Therefore, if it was desirable to make slits on the Battery section of the E-cigarette, one would need to redesign the entire E-cigarette so that the Battery section would be the female threaded portion and the Cartomizer section would be the male threaded portion. Additionally, one could never offer an option of interchanging the male Battery section between the Tip-Intake type with the Side-Intake type, while maintaining compatibility with the same female portion, since in the latter, the female Cartomizer would require slits at the engagement point, whereas in the former, the female Cartomizer could not have slits, otherwise the resulting airflow through the E-cigarette would be too great.

Accordingly, implementation of a Side-Intake Electronic Cigarette has, until the present invention, been considered an expensive and complicated proposition which would, by necessity, require redesign of all parts of the device and eliminate the possibility of backwards-compatibility of the majority of internal parts of the device.

SUMMARY

The present invention resolves the above problems and provide an air intake path from the side of the E-cigarette via modification to the male Battery connector, without modifying the female Cartomizer connector, while maintaining ease of manufacture—especially ease of machining the male Battery connector during mass production, and backwards compatibility whereas the same un-slited female Cartomizer could be used together with the male Battery connector for both the Tip-Intake and Side-Intake types of E-cigarettes.

The present invention also provides the possibility to create an air path that will allow a silent air intake, unlike other Side-Intake solutions that generate substantial hissing noise as the air enters from the side.

A cross-section of an Electronic Cigarette utilizing the Battery connector of the present invention is shown in FIG. 4. As can be seen there, the spaces 110 around the sensor are blocked so no air flow takes place through the cavity of the battery part. During inhalation, air 104 enters from the side 112 of the Battery and enters the post 108 of the Battery B via a groove in the battery post. It then enters into the Cartomizer A through the axial opening in the Cartomizer post and exits the Cartomizer into the smoker's mouth. Although there is also provided an opening 114 into the Battery through the battery post, there is minimal air or vapor flow through said opening 114 (hereinafter "pressure differential channel" 114) because the spaces 110 around the sensor are blocked. As a result, during inhalation, the sensor 102 can detect a pressure differential via said pressure differential channel 114.

During exhalation, the vapors do not enter into the battery part towards the sensor; they travel out through the side vents, opposite to the direction that air entered upon inhalation. Such a construction greatly extends the life of the product.

DESCRIPTION OF EMBODIMENTS

Figure 1:
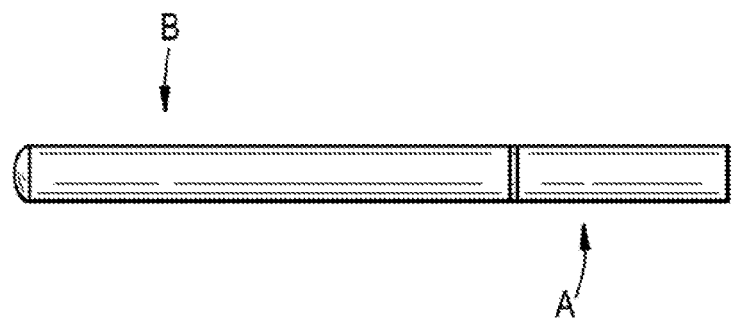
FIG. 1 is an assembled view of a typical two-piece electronic cigarette.
Figure 2:
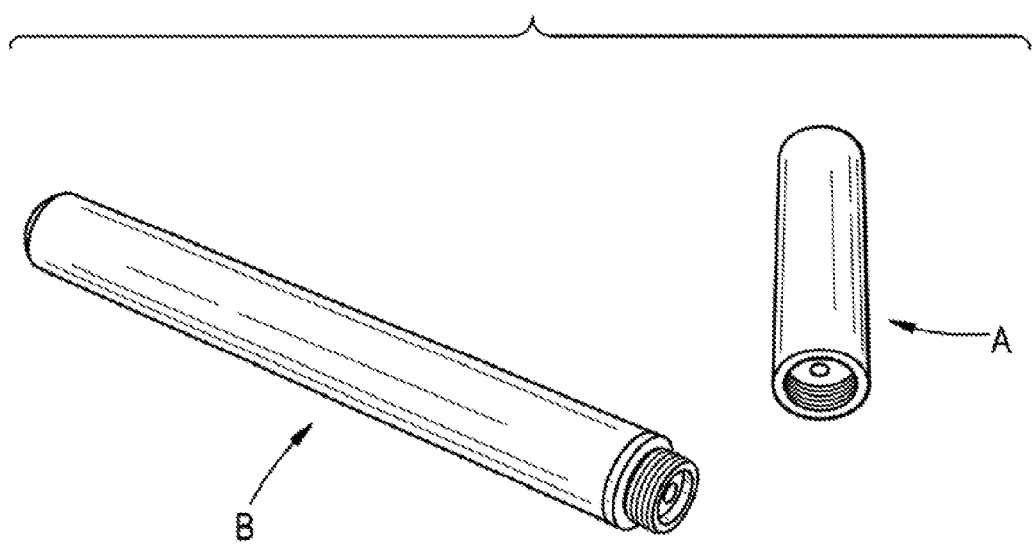
FIG. 2 is a disassembled view of a typical two-piece electronic cigarette.
Figure 3:
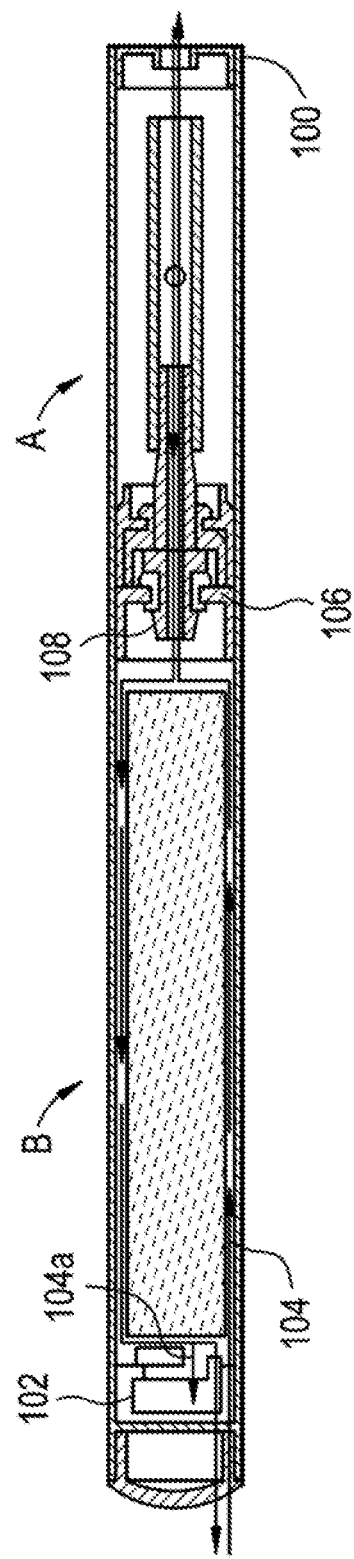
FIG. 3 is a cross-sectional view of an electronic cigarette in the prior art showing inhaled and exhaled air paths.
Figure 4:
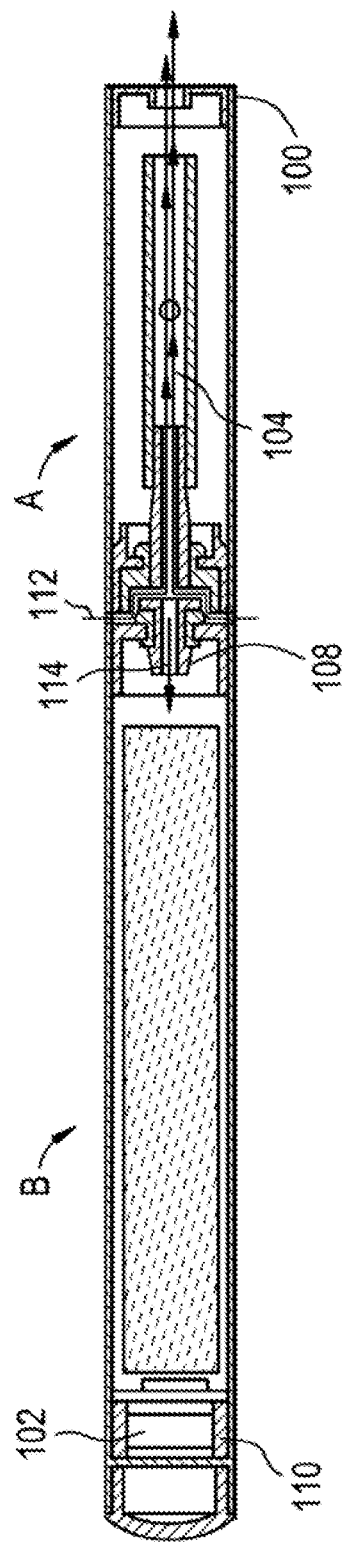
FIG. 4 is a cross-sectional view of an electronic cigarette using the novel connector herein described showing inhaled and exhaled air paths.

The present invention concerns various embodiments of a Battery-Cartomizer connector for an Electronic Cigarette that creates an air-intake path that enters through the male connector (i.e. the Battery section), without the need to modify the female connector (i.e. the Cartomizer section) thereof. Accordingly, the present invention permits flexibility of design and product diversification for the E-cigarette manufacturer, maintains ease of manufacture and mass-production, and creates additional advantages such as reducing noise and hissing during air-intake (i.e. a "puff or drag").

FIGS. 5-13 depict various embodiments of the connector of the present invention. It is understood that these figures depict a sectional view of an E-cigarette connector 1, which joins the Battery section to the Cartomizer section by a threaded engagement. As shown in FIGS. 5-13, it is intended that the male Battery connector M at the proximal end 3 of the connector mates to a female portion of a Cartomizer, and the distal end 5 of the connector is attached, through a pressure or friction fit, or through other suitable means, to the Battery portion B (not shown) and functions as a "cap" thereof.

In some embodiments of the present invention, an air intake path starts at the outer circumference of the connector 1 between the Battery and the Cartomizer of the E-cigarette, running inside notch 9 on connector 1. The air is thus brought into the Battery through grooves 10 formed on the attachment (i.e., non-threaded) distal end 5 of the connector. Once inside the battery, the air path loops around and exits the Battery housing towards the Cartomizer, via a hole along the central axis of connector 1. In accordance with the desired air-intake path, notch 9 is cut out on the side of connector 1 at strategic location and with strategic geometry.

In most E-cigarettes, connector 1 has a flange 7 that appears from the outside as a metallic ring when the separate parts of the E-cigarette are screwed together, like that shown in FIG. 1. The resulting ring is usually very thin, and has little purpose other than cosmetic—to create a decorative divider between the two major parts of the E-cigarette (i.e. the Battery section and the Cartomizer section) and to cover the inside edge of the Battery housing. Cutting into this ring or removing a portion of it to create the desired air-intake characteristics of the present invention would expose the dull edge of the Battery housing and detracts from the esthetics of the product. However, in some embodiments of the present invention, the thickness of the flange is increased so that a portion of it can be cut or milled away, resulting in notch 9, while the remaining portion of the flange thickness will still retain the aesthetic design and still cover the internal edge of the housing.

Figure 5:
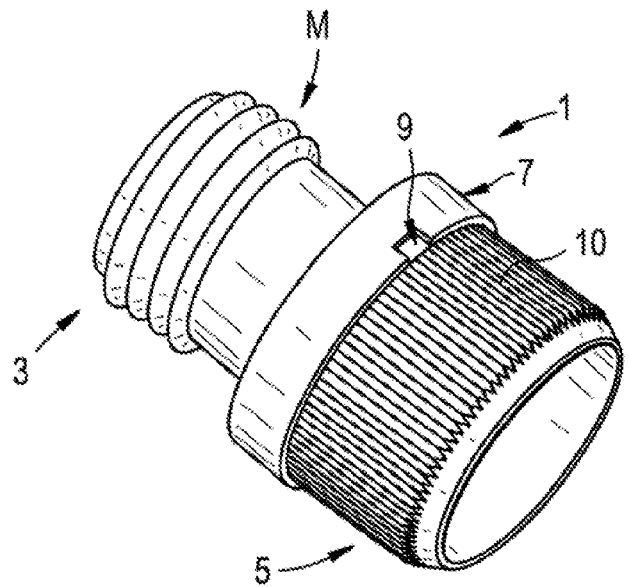
FIGS. 5-13 are alternative embodiments of the connector of the present invention showing various arrangements of side vent apertures.

Accordingly, as shown in FIG. 5, in some embodiments of connector 1, notch 9 begins at the outer perimeter of the flange 7, toward distal end 5 and travels toward the center axis of flange 7, resulting in a rectangular shape.

Figure 6:
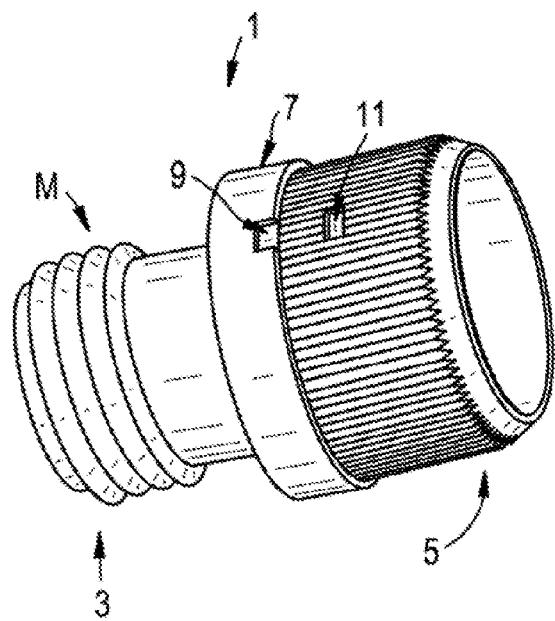

In some embodiments, such as in FIG. 6, aperture 11 is bored through the wall of the distal end 5 of connector 1 at substantially the same radial location as notch 9. This configuration increases the air-intake volume, permitting less-constricted air flow through the connector 1 and the Battery section.

Figure 7:
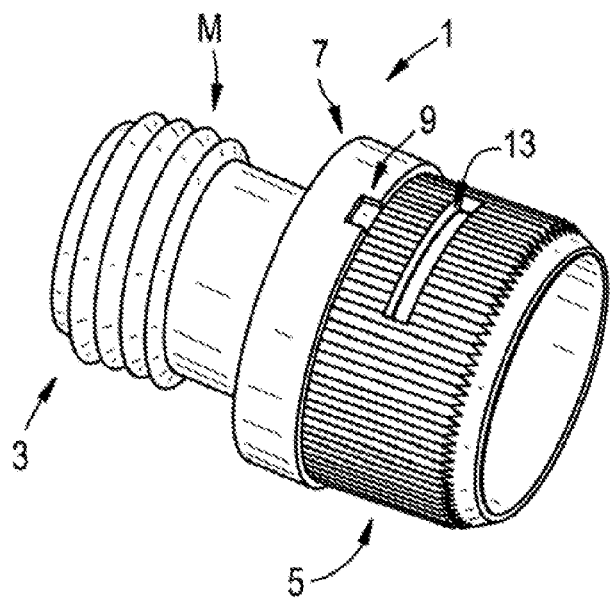

In some embodiments, such as in FIG. 7, slot 13 is milled along the curved wall of the distal end 5 of connector 1, with notch 9 located substantially across from the center of slot 13, radially. As shown, slot 13 is oriented perpendicular to the longitudinal axis of connector 1.

Figure 8:
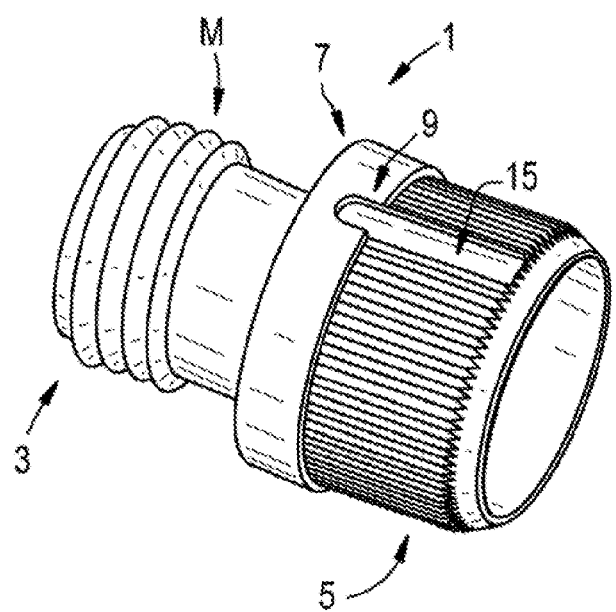

In some embodiments, such as in FIG. 8, channel 15 is milled across the outer surface of the distal end 5 of connector 1, beginning at notch 9 and terminating at the end of distal end 5. In this configuration, notch 9 has a substantially curved profile that transitions uniformly into channel 15. In this configuration, channel 15 is milled substantially parallel to the longitudinal axis of connector 1.

Figure 9:
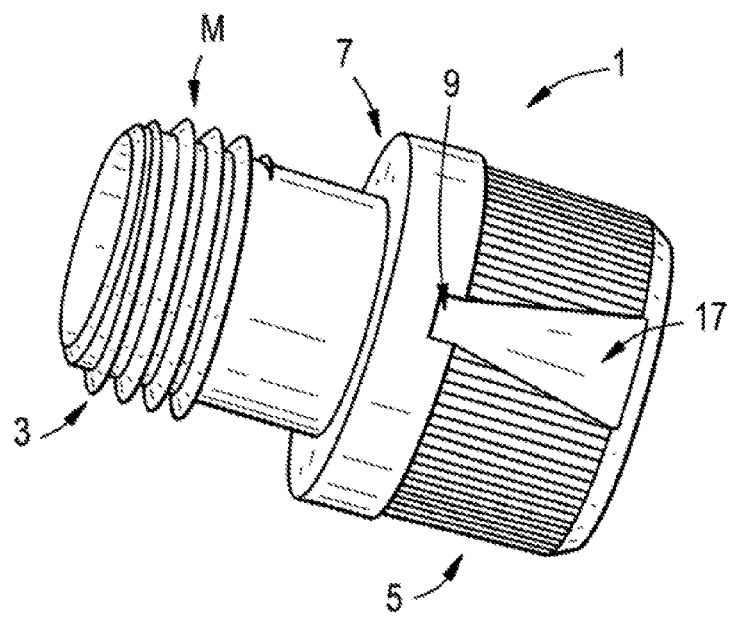

In some embodiments, such as in FIG. 9, fanned channel 17 is milled across the outer surface of the distal end 5 of connector 1, beginning at notch 9 and terminating at the end of distal end 5. Notch 9 has a substantially curved profile that transitions into fanned channel 17. Fanned channel 17 is milled substantially parallel to the longitudinal axis of connector 1.

Figure 10:
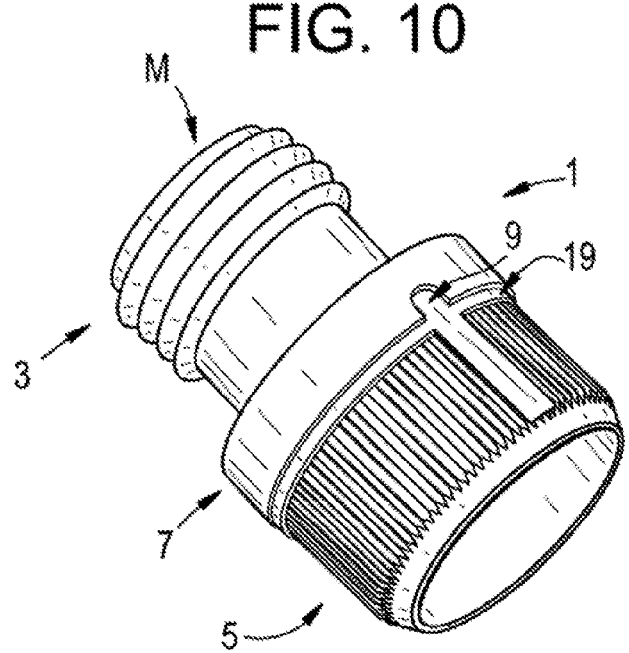

In some embodiments, such as in FIG. 10, channel 19 is milled away all around the outer circumference of flange 7, along its distal edge. The purpose of channel 19 is to allow for air intake even when a user happens to hold his finger over notch 9 during smoking. When that happens, air enters channel 19 and runs along the channel until it reaches and enters notch 9.

Figure 11:
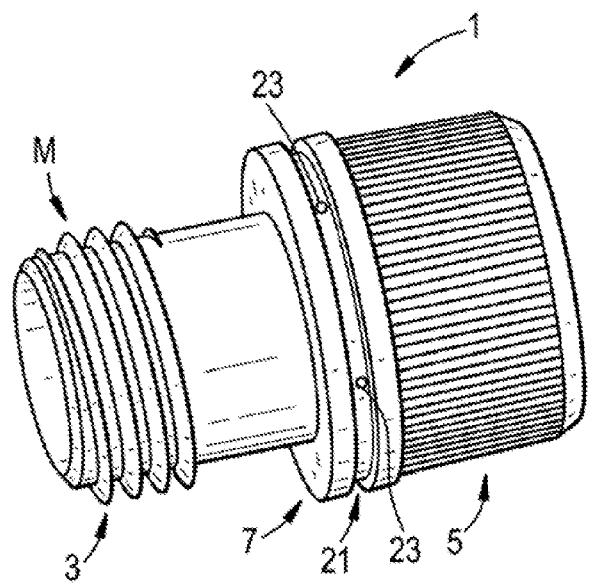

In some embodiments, such as in FIG. 11, channel 21 is milled away all around the outer circumference of flange 7, substantially in the middle of the flange. Several apertures 23 are bored through the wall of the flange. The purpose of channel 21 is to allow for air intake even when a user holds his finger over an aperture 23 during smoking. When that happens, air enters channel 21 and runs along the channel until it reaches and enters an aperture 23.

Figure 12:
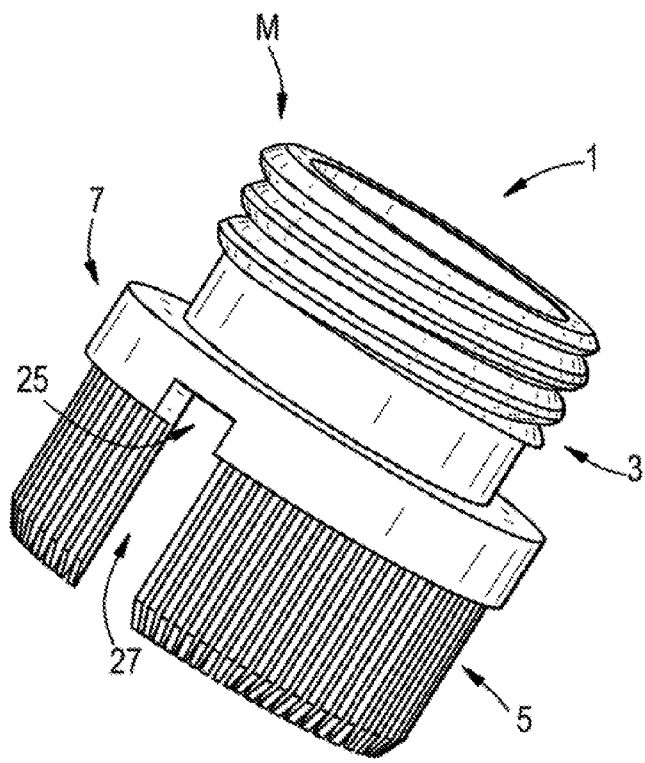

In some embodiments, such as in FIG. 12, notch 25 is cut out through the wall of flange 7 on the side of connector 1 at strategic location and with strategic geometry. Slot 27 is cut out of the distal end 5 of connector 1, beginning at notch 25 and terminating at the end of distal end 5. In this configuration, notch 25 has a rectangular profile that transitions uniformly into slot 27.

Figure 13:
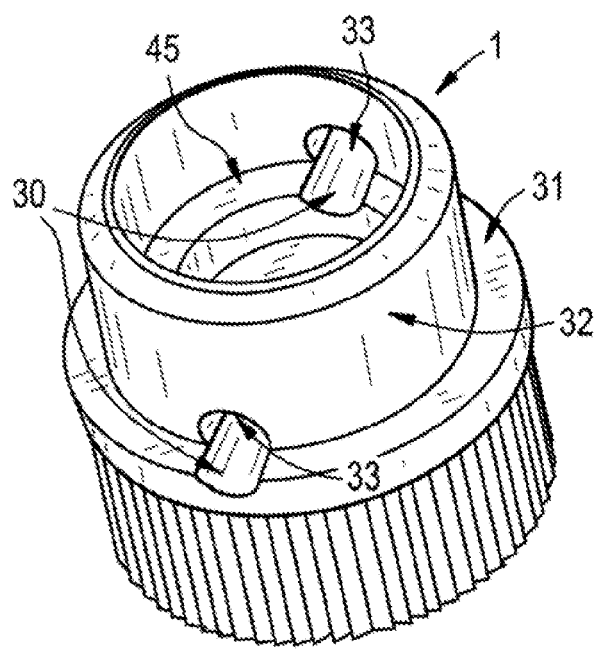
Figure 14:
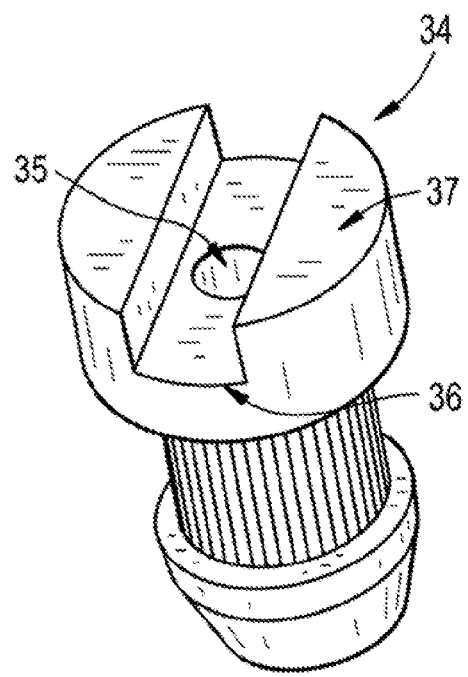
FIGS. 14-15 illustrate an alternative embodiment of a connector of the present invention with a battery post of the present invention.
Figure 15:
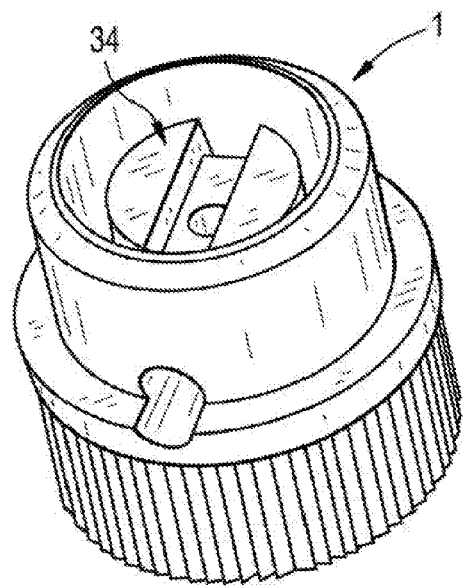

Another embodiment of the connector of the present invention is shown in FIGS. 13-15. FIG. 13 shows the connector without a battery post, FIG. 14 shows the battery post and FIG. 15 shows the battery post and connector assembled. As shown in FIG. 13, instead of a notch in the outer perimeter of the flange 7, toward distal end 5, perpendicular surface channels 30 are drilled on shelf 31 of flange 7. The channels continue and penetrate through the shaft 32 of connector 1 (in which threads are not shown for purposes of clarity) at orifices 33 and continue through inner shelf 45. The engaging battery post 34, shown in FIG. 14, includes a longitudinal orifice 35 (beginning on the surface of post head 37 and continuing longitudinally completely through the post) that forms the pressure differential channel, as well as a groove 36 which assists in guiding air inhaled or exhaled through perpendicular surface channel 30 and orifice 33.

It should be noted here that although in FIG. 15 groove 36 is shown aligned with perpendicular surface channel 30 and orifice 33, because the outer diameter of post head 37 is smaller than the inner diameter of shaft 32, such alignment is not necessary to allow for unimpeded air flow through connector 1.

Figure 16:
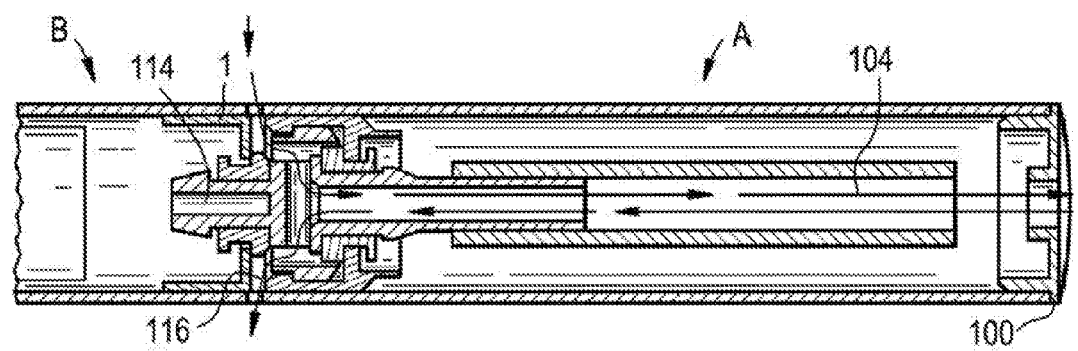
FIG. 16 is a cross-sectional view of an electronic cigarette using the connector and battery post shown in FIGS. 13-15.

The airflow 104 through the connector and battery post combination shown in FIGS. 13-15 is illustrated in FIG. 16. As shown in FIG. 16, one possible draw-back of this arrangement is that upon exhalation, any excess fluid 116 (vapor, saliva, etc.) could be blown through orifice 35, into the pressure differential channel and into the Battery B.

Figure 17:
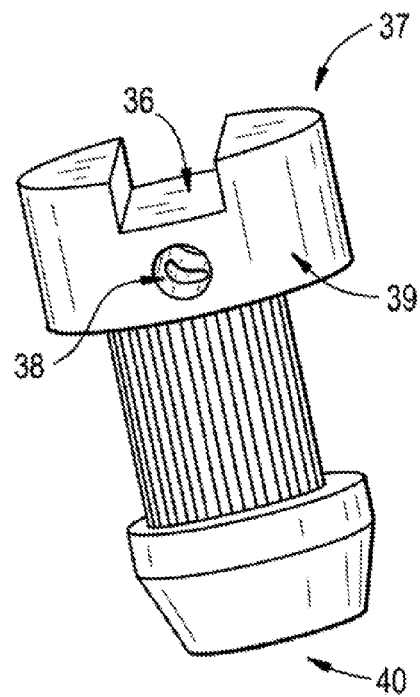
FIG. 17 illustrates an alternative embodiment of a battery post of the present invention.

An alternative embodiment for a battery post designed to minimize this problem is shown in FIG. 17. As shown in this figure, there is no orifice drilled through post head 37. Rather, the air path to the pressure differential channel is created by channel 38 which is drilled beneath groove 36 on the side 39 of post head 37. Channel 38 perpendicularly intersected by the pressure differential channel (not shown) which is drilled longitudinally from battery post end 40.

Figure 18:
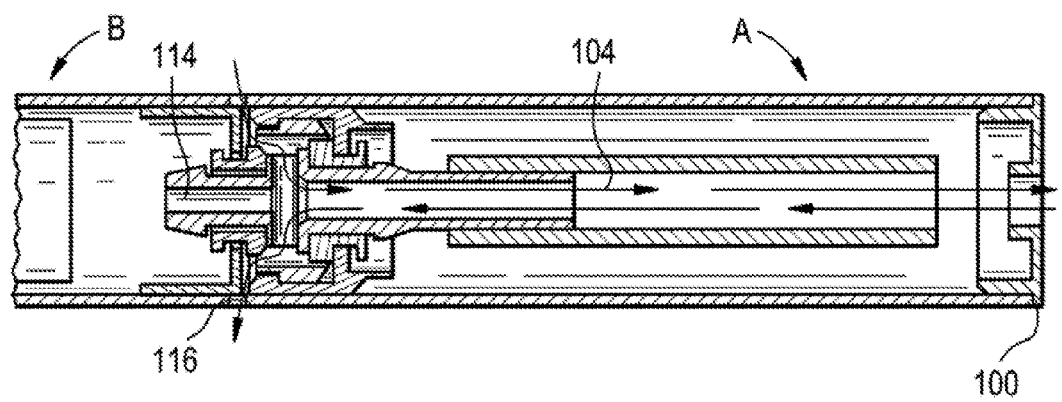
FIG. 18 is a cross-sectional view of an electronic cigarette using the connector of FIG. 13 and the battery post of FIG. 17.

The airflow through a connector such as that shown in FIG. 13 using the battery post shown in FIG. 17 is illustrated in FIG. 18. As is shown in this figure, there is no direct path for excess liquid 116 to migrate into the Battery compartment B.

The connector 1 of the present invention has an additional major advantage in that those embodiments shown in FIGS. 5-18 allow for a substantially silent air-intake without the excessive hissing or noise associated with other known E-cigarettes. Another major advantage of the present invention is its application in newly introduced V-Go and E-go (large-capacity electronic cigarettes) E-cigarettes. V-go and E-go E-cigarettes, which almost always have a side-intake, cannot be used with non-vented female Cartomizers. Heretofore manufacturers always had to resort either to vented female Cartomizers or non-vented male Cartomizers. However, with the present invention, it is possible to create V-go and E-go E-cigarettes that will be interchangeable with Tip-Intake E-cigarettes so that they are compatible with the same existing female unvented Cartomizers, without the need to modify the Cartomizers.

It should be appreciated that although the above-described embodiments demonstrate that some embodiments of the present invention are designed such that the Battery comprises the "male" connection and the Cartomizer comprises the "female" connection, the reverse configuration may be equally suitable, depending on design requirements. Accordingly, the Cartomizer may comprise the "male" connection and the Battery may comprise the "female" connection.

It will be understood that the preferred embodiments of the present invention have been disclosed by way of example and that other modifications and alterations may occur to those skilled in the art without departing from the scope of the disclosure herein.

The invention claimed is:

1. A cylindrical connector configured to couple a first section and a second section of an e-vaping device, comprising:
    a major body with a proximal portion and a distal portion, the major body defining a longitudinal channel through a longitudinal length of the major body from the proximal portion through the distal portion, the proximal portion including a shaft with side walls that define an external screw thread; and
    a flange having a first external surface and being located between the proximal portion and the distal portion, the flange at least partially defining at least a first portion of at least one first aperture in fluid communication with the longitudinal channel, the flange being spaced apart from the external screw thread.

2. The cylindrical connector of claim 1, wherein an outer shelf exists on the major body due to a difference in an external diameter between the shaft and the flange, the shelf facing the proximal portion of the major body.

3. The cylindrical connector of claim 2, wherein the first section includes a battery section and the second section includes a cartridge.

4. The cylindrical connector of claim 2, wherein the distal portion of the major body has a second external surface, the second external surface defining a plurality of longitudinal grooves formed along at least a portion of a longitudinal length of the distal portion.

5. The cylindrical connector of claim 2, wherein the at least one first aperture includes two or more apertures spaced evenly along the first external surface of the flange.

6. The cylindrical connector of claim 2, wherein the first external surface of the flange constitutes a section of the major body, along the longitudinal length of the major body, which is a largest external diameter of the major body.

7. The cylindrical connector of claim 2, wherein a diameter of the distal portion of the major body is larger than a diameter of the proximal portion of the major body, and a diameter of the flange is larger than the diameter of the distal portion of the major body.

8. The cylindrical connector of claim 2, wherein the distal portion of the major body has a first end and a second end, the first end of the distal portion being directly connected to the flange, and the second end of the distal portion being beveled.

9. The cylindrical connector of claim 2, wherein the first external surface defines a groove that exists along at least a portion of the flange, the first external surface being a first circumferential outer surface.

10. The cylindrical connector of claim 9, wherein the shaft has a first end and a second end, the first end of the shaft being connected to the flange, and the second end of the shaft defining the external screw thread.

11. The cylindrical connector of claim 2, wherein the outer shelf and the side wall of the shaft combine to collectively define the first portion of the at least one first aperture.

12. The cylindrical connector of claim 11, further comprising:
an inner shelf positioned along an interior circumferential surface of the shaft, the inner shelf facing the proximal portion of the body.

13. The cylindrical connector of claim 12, wherein the inner shelf at least partially defines a second portion of the at least one first aperture.

14. The cylindrical connector of claim 13, wherein the inner shelf and outer shelf collectively define a rounded trough, the rounded trough forming a side wall of the at least one first aperture.

15. The cylindrical connector of claim 1, wherein the distal portion of the major body is configured to attach to the first section of the e-vaping device and the proximal portion of the major body is configured to attach to the second section of the e-vaping device in order to define an airflow path that enters the longitudinal channel through the at least one first aperture and flows through the proximal portion of the major body while the e-vaping device is in operational use.

16. A cylindrical connector configured to couple a first section and a second section of an e-vaping device, comprising:
a major body with a proximal portion and a distal portion, the major body defining a longitudinal channel through a longitudinal length of the major body from the proximal portion through the distal portion, the proximal portion including a shaft with side walls that define an external screw thread; and
a flange having a first external surface and being located between the proximal portion and the distal portion, the flange at least partially defining at least a first portion of at least one first aperture in communication with the longitudinal channel, the flange being spaced apart from the external screw thread,
wherein an outer shelf exists on the major body due to a difference in an external diameter between the shaft and the flange, the shelf facing the proximal portion of the major body, the first external surface defining a groove that exists along at least a portion of the flange, the first external surface being a first circumferential outer surface, and the groove being an annular groove that exists around the entire first circumferential outer surface of the flange.

17. The cylindrical connector of claim 16, wherein a first entrance of the at least one first aperture is embedded within the groove.

18. A cylindrical connector configured to couple a first section and a second section of an e-vaping device, comprising:
a major body with a proximal portion and a distal portion, the major body defining a longitudinal channel through a longitudinal length of the major body from the proximal portion through the distal portion, the proximal portion including a shaft with side walls that define an external screw thread; and
a flange having a first external surface and being located between the proximal portion and the distal portion, the flange at least partially defining at least a first portion of at least one first aperture in communication with the longitudinal channel, the flange being spaced apart from the external screw thread,
wherein an outer shelf exists on the major body due to a difference in an external diameter between the shaft and the flange, the shelf facing the proximal portion of the major body, the first external surface defining a groove that exists along at least a portion of the flange, the first external surface being a first circumferential outer surface, and the shaft having a first end and a second end, the first end of the shaft being connected to the flange and having a third external surface, the second end of the shaft having a fourth external surface that defines the external screw thread, the fourth external surface having a larger external diameter than the third external surface.

* * * * *